United States Patent [19]

Markle et al.

[11] Patent Number: 5,280,130
[45] Date of Patent: Jan. 18, 1994

[54] ASSEMBLY OF A TUBE AND A PART AND APPARATUS AND METHOD OF MANUFACTURE

[75] Inventors: David R. Markle, Paoli, Pa.; William Paterson, High Wycombe, England

[73] Assignee: Biomedical Sensors, Ltd., High Wycomb, England

[21] Appl. No.: 887,993

[22] Filed: May 22, 1992

[51] Int. Cl.⁵ .............................................. F16B 4/00
[52] U.S. Cl. ........................................ 174/1; 128/634; 174/DIG. 8; 403/273
[58] Field of Search ............ 174/1, DIG. 8; 128/634; 403/273

[56] References Cited

U.S. PATENT DOCUMENTS

| | | | |
|---|---|---|---|
| Re. 31,879 | 5/1985 | Lübbers et al. | 436/133 |
| 4,200,110 | 4/1980 | Peterson et al. | 128/634 |
| 4,469,357 | 9/1984 | Martin | 285/381 |
| 4,754,538 | 7/1988 | Stewart, Jr. et al. | 29/157.4 |
| 4,889,407 | 12/1989 | Markle et al. | 350/96.29 |
| 5,005,576 | 4/1991 | Günther | 128/634 |
| 5,047,208 | 9/1991 | Schweitzer et al. | 422/58 |
| 5,047,627 | 9/1991 | Yim et al. | 250/227.23 |

*Primary Examiner*—Leo P. Picard
*Assistant Examiner*—D. A. Tone
*Attorney, Agent, or Firm*—Peter C. Richardson; Lawrence C. Akers; Mark Dryer

[57] ABSTRACT

An apparatus for assembling a tube and a part has a polymeric tube with an axis along the longitude thereof. The part has a cross sectional shape and size to be near an inside surface of the tube when the part is at least partially therewithin. The part or tube is supported so that relative movement along the axis places the part at least partially within the tube located between the ends or in the tube near the distal or proximal end thereof. The part and/or the tube is a thermoplastic polymer made by a process that develops within the polymer a memory of the polymer prior to forming so that residual stresses remaining in the part can be relaxed by changing temperature causing expansion. A form of a relatively nonconductive material is positioned for relative movement along the axis and for placement about the tube. The form is shaped and sized to fit and contain the outside surface of the tube. A heater has an electrically resistive element wrapped about the form for changing the temperature of the tube and the part. A method of assembly of the tube has the steps of supporting it and/or the part for relative movement along the axis placing the part at least partially within the tube, positioning the form for relative movement along the axis for placement about the tube whereinside the part is located to thereby contain the outside surface, changing the temperature of the tube and the part sufficiently to relax residual stresses of the manufacturing processes used to make the tube and/or the part for causing engagement of the inside surface of the tube and the part.

15 Claims, 4 Drawing Sheets

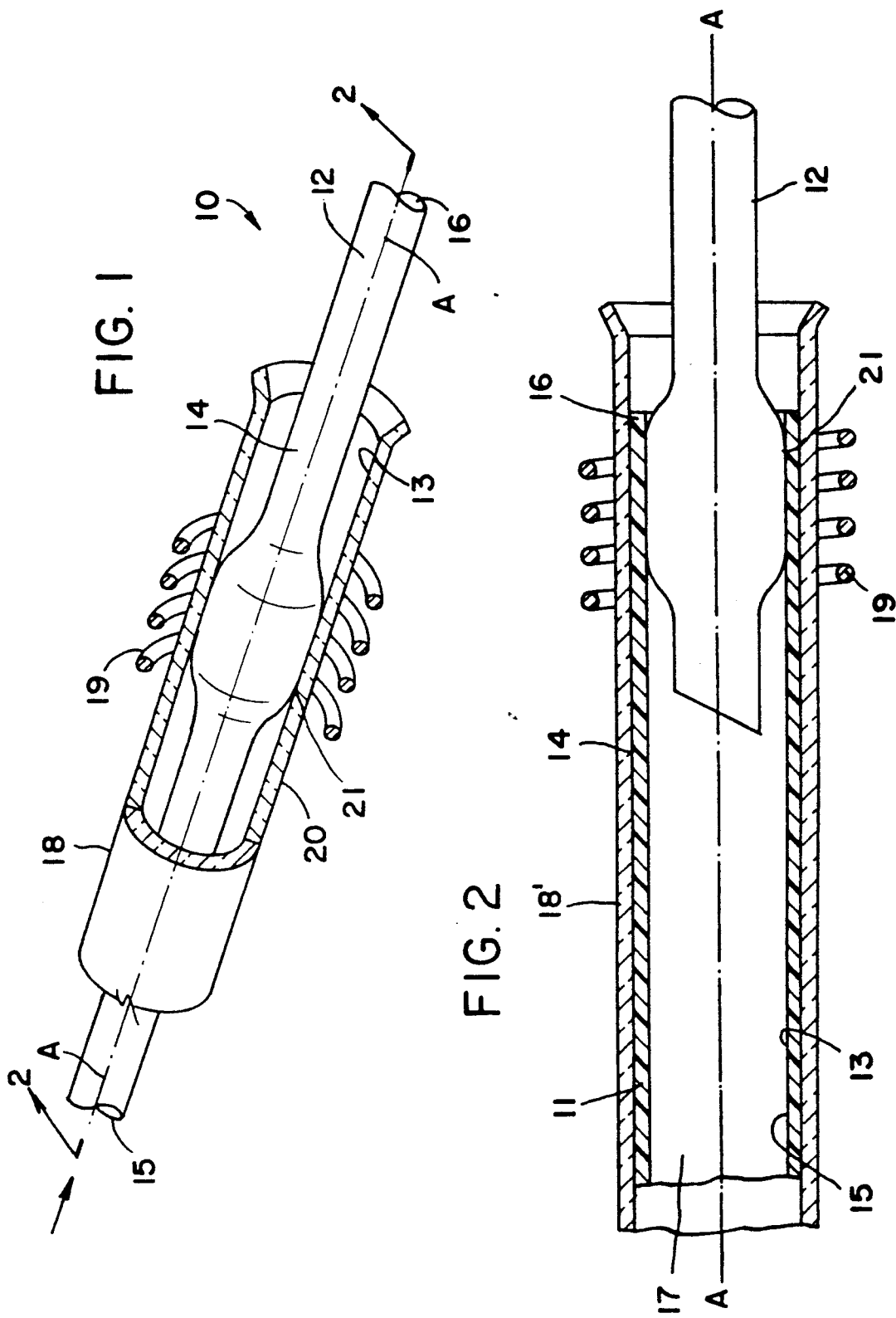

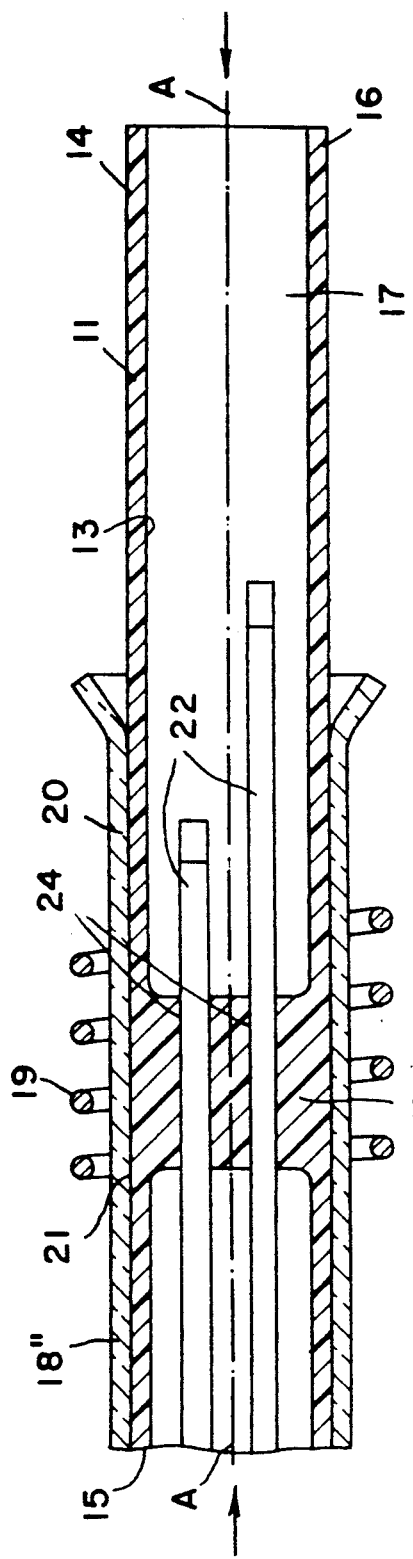
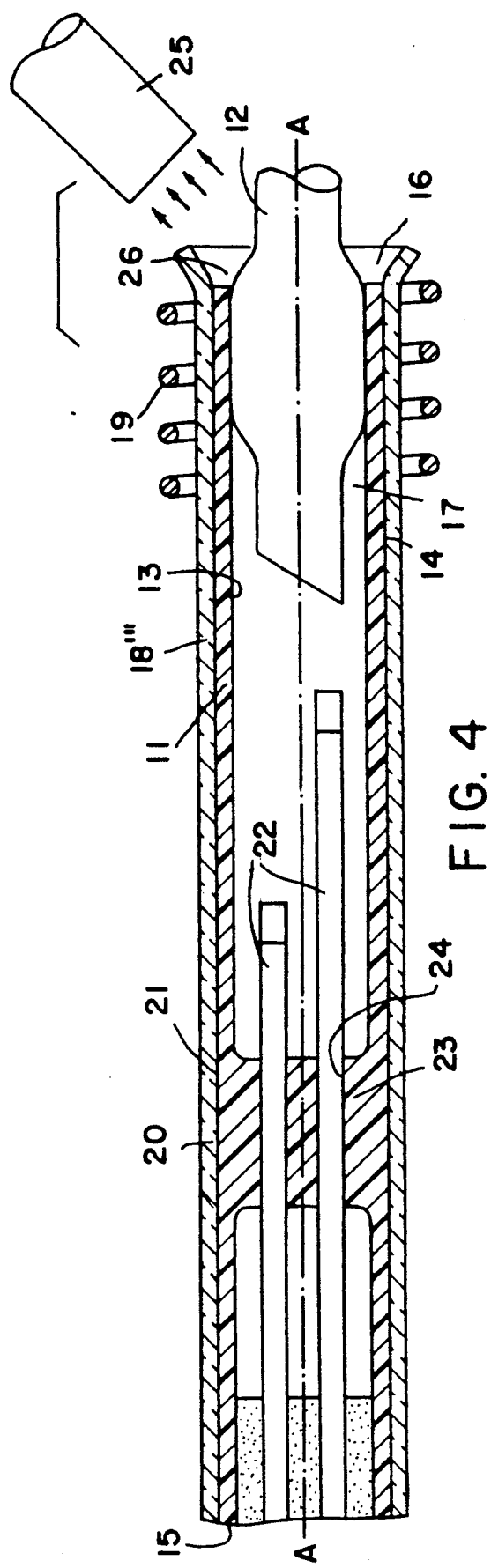
FIG. 3
FIG. 4

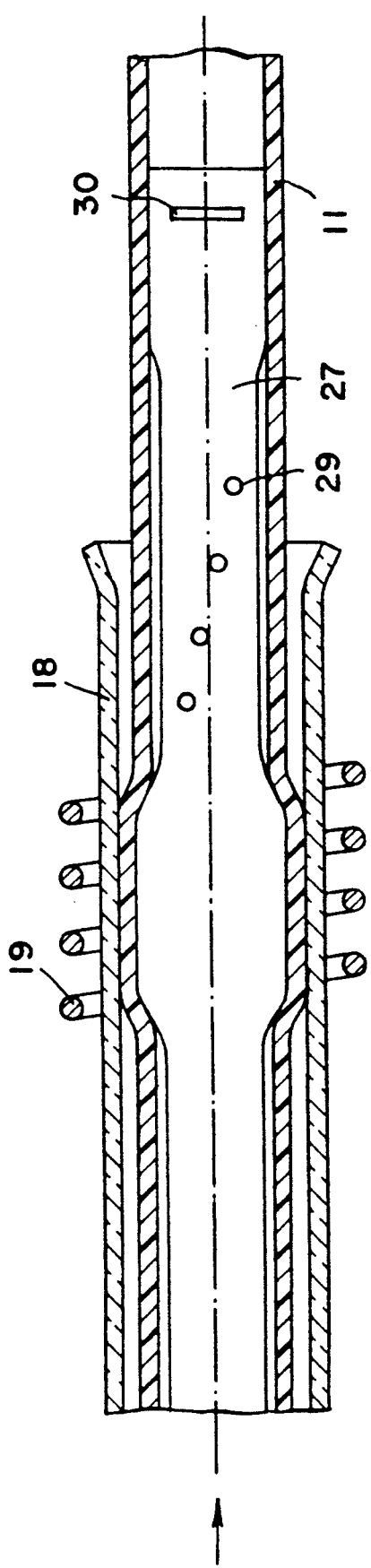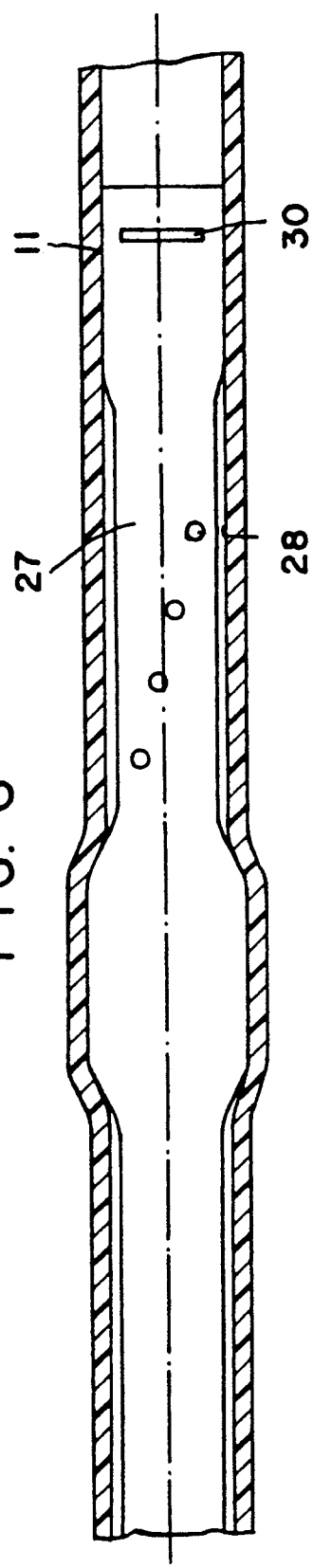

ASSEMBLY OF A TUBE AND A PART AND APPARATUS AND METHOD OF MANUFACTURE

1. FIELD OF THE INVENTION

This invention relates to an assembly of, an apparatus for and a method of assembly of a tube and a part located at least partially within the tube. More particularly, relaxation of residual stresses or release of the memory of the manufacturing process used to make the part allow expansion of the part for engagement of the tube.

2. BACKGROUND OF THE DISCLOSURE

Described herein are an assembly of, an apparatus for and a method of assembly of a tube and a part located at least partially within the tube. Release of residual stresses so the memory of the manufacturing process used to make the part and the tube permits expansion thereof for engagement therebetween that is not found in the literature or practiced in the field. The literature is of interest for its teachings of the knowledge of skilled artisans at the time of this invention of an assembly of, apparatus for and method of assembly of a tube and a part located at least partially therewithin. The assembly of microscopic sized tubes and parts presents additional difficulties.

Typically tubes are stoppered, plugged or sealed by application of a press fit, shrink fit or wedging component into the bore thereof. Chemicals such as adhesives, sealants or glues are frequently applied to make a fluid tight joint. The accurate application of chemicals to make a small joint fluid tight presents added difficulties of placement and clean up. Often the chemicals used can interfere with the operation of the assembly being made therewith.

Optical fibers or fiber optic chemical sensor used in vivo as probes must be sensitive to slight changes in gas or ion concentrations. Chemicals can also leach into the blood stream. For example, U.S. Pat. No. 4,200,110 has a fiber optic probe with an ion permeable membrane enclosure about the distal ends of a pair of fiber optics. Change in color of a pH sensitive dye is detected. The addition of sealants and the like is something to be avoided.

U.S. Pat. No. Re 31,879 has a method for measuring concentration of an analyte in a sample that changes color and/or the intensity of light emitted from a fluorescent indicator attached to the fiber. U.S. Pat. No. 5,047,208 has an optical sensor for blood gas measurement with a pH sensitive absorption dye between the end of the fiber and the mirror. The mirror is located by a tube which carries a mirror spaced from and coaxially aligned with the fiber so the dye can be in the space. These and other patents are typical of the microscopic constructions required for in vivo blood analysis and the manner in which structures have been made.

U.S. Pat. No. 5,005,576 has an optical sensor for blood gas measurement capable of measuring pH and $pCO_2$ with light absorption dyes between the end of the fiber and the mirror. The mirror is located in the distal end of the sheath with a silicone glue to close off the end of the probe.

U.S Pat. No. 5,047,627 has an optical sensor for blood gas measurement capable of measuring pH, $pO_2$ and $pCO_2$ with light absorption or fluorescent dyes between the ends of the fibers and the mirrors. The mirrors attached to the dye pellet for each fiber with glue and seal the fiber end. Certainty and consistency of assembly is not always repeatable with adhesive attachment and chemicals in the adherent may adversely influence the chemistry of the sensor and therefor measurement accuracy.

U.S. Pat. No. 4,889,407 has an optical fiber with arrayed cells to substantially cover the cross sectional area of the fiber. An indicator sensitive to an analyte in a medium is used to determine pH and $pCO_2$ in vivo in blood. That commonly assigned patent is incorporated herein by reference since the disclosure herein may be applicable to that fiber distal end.

SUMMARY OF THE INVENTION

An apparatus for assembling a tube and a part preferably has a tube which has an axis along the longitude thereof, inside and outside surfaces and proximal and distal ends. The tube preferably has an internal cross sectional shape identical to the part and a cross sectional size larger than the part prior to changing temperature. The part may have an external cross sectional size identical to the internal cross sectional size of the tube after change in temperature. The tube may have an internal circular cross sectional shape defined by a bore through the tube and the part may have a circular cross sectional shape of a diameter that allows axial movement within the tube.

The part should preferably have a cross sectional shape and size to be near the inside surface upon placement of the part at least partially within the tube. The part or the tube may be supported so that relative movement along the axis places the part at least partially within the tube. The part is preferably made of a thermoplastic polymer by a process that develops within the polymer thereof a memory of the unshaped thermoplastic polymer prior to forming into the cross sectional shape of the part so that residual stresses remaining in the formed part are relaxed by changing temperature causing expansion of the cross sectional size of the tube and/or the part. The part is preferably made by an extrusion process to develop memory. The part may be located in the tube between the ends thereof, located in the tube near the proximal or distal end thereof.

A form is preferably made of a relatively nonconductive material and is preferably positioned for relative movement along the axis for placement about the tube whereinside the part is located. The form might be shaped and sized to fit the tube outside surface and contain it. The form, the tube and the part can be generally circular.

A heater is preferably made of an electrically resistive element wrapped about the form and is associated therewith for changing the temperature of the tube and the part sufficiently to relax residual stresses of their respective manufacturing processes used to make the tube and the part and thereby cause engagement of the inside surface and the part. The heater changes the temperature beyond the glass transition point of the polymer allowing the combined tube and part to expand to the identical cross sectional size of the internal cross section of the form and to remain expanded thereafter. Engagement as used herein means that if the part and tube are made of materials that are heat sealable with respect to one another, then they will fuse together when the meet. Alternatively, if the materials will not fuse then they form a tight fit therebetween upon engagement.

A method of assembly of a tube with an axis along the longitude thereof and with inside and outside surfaces and proximal and distal ends and a part with a cross sectional shape and size to be near the inside surface when the part is at least partially within the tube includes a form shaped and sized to fit about the tube outside surface and a heater associated with the form. The method may preferably include the steps of supporting the tube or the part so that relative movement along the tube axis places the part at least partially within the tube. Then the step of positioning the form for relative movement along the axis for placement about the tube whereinside the part is located thereby contains the outside surface. Changing the temperature of the tube and the part sufficiently relaxes residual stresses of the manufacturing process respectively used to make the tube and the part for causing engagement of the inside surface of the tube and the part.

The method may also include the added steps of placing the part in the distal end of the tube displaceing liquid, clearing the space around the part and the tube of the displaced liquid and conducting sufficient heat through the form into the part to form a seal therebetween. The step of clearing is performed by drawing displaced liquid by most preferably applying a vacuum near the part during placement.

BRIEF DESCRIPTION OF THE DRAWINGS

FIG. 1 is a perspective view partially in cross section of an apparatus for expanding a part located at least partially within a form.

FIG. 2 is a side view in cross section of a distal end of a tube with the part located at least partially therewithin for plugging the distal end of the tube; the form is about the tube whereinside the part is located.

FIG. 3 is a side view in cross section of a pluralities of conductors extending through a radially expanded section positioned within a tube to illustrate sealing to the tube and the conductors as the first step in the assembly of a sensor catheter.

FIG. 4 is a side view in cross section of the sealed conductors, radially expanded section and tube wherein the distal end thereof is sealed with a part while a vacuum is drawn to clear the area around the sensors.

FIG. 5 is a side view in cross section of an optic fiber extending through a tube to illustrate sealing between the tube and the fiber as a step in the assembly of a sensor catheter.

FIG. 6 is a side view in cross section of the sealed fiber, radially expanded within the tube wherein the fiber is expanded tightly against the inside of the tube.

DETAILED DESCRIPTION OF THE INVENTION

Figure 7:
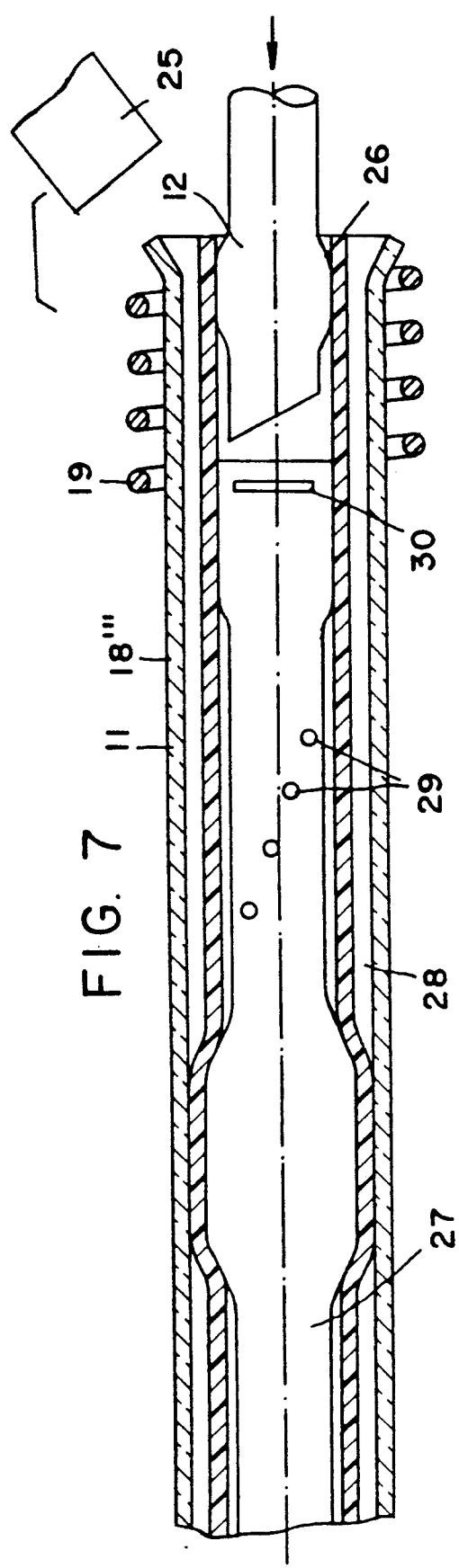
FIG. 7 is a side view in cross section of the sealed fiber, radially expanded section and tube wherein the distal end thereof is sealed with a part while a vacuum draws liquid displaced when the part is pushed into the distal end of the tube.

An apparatus 10 for and a method of assembly of a tube 11 and a part 12 located at least partially within the tube 11 by relaxation, of residual stresses or release of the memory of the manufacturing process used to make the part 12 allows expansion of the tube 11 and the part 12 for engagement therebetween are disclosed and claimed. The claims are not limited to the structure for the assembly or apparatus 10 described and illustrated by way of example and the methods of manufacture specifically disclosed. The claims are to be considered in view of the existing knowledge of skilled artisans in the Field prior to the inventions defined by the language of the claims herein as amended or considered in view of knowledge of skilled artisans prior to these inventions.

The particular and most preferred application of the technology disclosed and claimed herein is for the construction of a small (less than 20 gauge) blood gas sensor catheter like those mentioned in the background hereof. Specifically the sealing of the distal portion of the blood gas sensors within a vascular catheter sheath about conductors such as electrical wires and/or optic fibers passing axially therethrough and the termination of the leading end of the blood gas catheter.

FIG. 1 is a perspective view partially in cross section of the apparatus 10 for expanding and the part 12 located at least partially within a form 18. The part 12 is formed of a polymeric monofilament in the preferred embodiment which extends along an axis A. Specifically, amid the heating process the monofilament is as necessary urged axially toward the area of heating within the form 18 to encourage thickening and result in a larger section as shown. Urging the monofilament is in the preferred embodiment accomplished by feeding the monofilament axially toward the area of heating from either direction; that is, each end is pushed toward the middle with sufficient force to provide thickening.

Referring to FIG. 2 wherein the tube 11 includes an inside surface 13 and an outside surface 14 extending between a proximal end 15 and a distal end 16. Preferably tube 11 is used as a sheath for a blood gas sensor used in a vascular catheter and has an internal cross sectional shape identical to the part 12 and a cross sectional size slightly larger than the part 12 prior, as will be explained in detail herein, to changing temperature. The part 12 may take various forms, as will be disclosed and explained, but it is preferred that the part 12 have an external cross sectional size substantially identical to the internal cross sectional size of the tube 11 after change in temperature in that way sealing therebetween is achieved.

In the preferred embodiment, i.e. a blood gas sensor for a vascular catheter, the tube 11 may have an internal circular cross sectional shape defined by a bore 17 through the tube 11. Similarly, the part 12 may have a circular cross sectional shape of a diameter that may allow axial movement within the tube 11 prior to sealing. The part 12 should preferably have a cross sectional shape and size to be substantially near the inside surface 13 upon placement of the part 12 at least partially within the tube 11. It is desired that the part 12 if used to seal the distal end 16 be slightly tapered to displace any liquid in the tube 11 so that a bubble free fill remains when the part 12 and tube 11 are sealed.

An apparatus for assembly of the tube 11 and the expanded section 12 supports the part 12 and/or the tube 11 for relative movement along the axis A placing the part 12 at least partially within the tube 11. The precision and speed necessary to place the part 12 within the tube 11 is easily accomplished by automatic machinery that aligns the part 12 and the tube 11 with the axis A so that each is centered and can be placed concentric to one another.

In FIG. 1 the part 12 is shown as the preferred monofilament which can be fed into and through the form 18 from either the proximal or distal ends 15 or 16 in accord with the desired result. The part 12 is expanded in the form 18 by application of heat so that it may be located in the tube 11 between the proximal or distal ends 15 or 16 thereof or located in the tube 11 near the proximal or distal ends 15 or 16 thereof for plugging.

FIG. 2 is a side view in cross section of the form 18' used for assembly of the tube 11 and the part 12 (as reformed in a form 18) and wherein now the part 12 is shown located at least partially within the distal end 16 of the tube 11. The part 12 is inserted into the distal end 16 not through the tube 11 although that is a possible option. The part 12 and/or the tube 11 are in the preferred embodiment each made of a thermoplastic polymer by a process that develops within the polymer of each a memory of the unshaped thermoplastic polymer prior to forming into the cross sectional shape of the part 12 and/or the tube 11. While the part 12 and the tube 11 may be the same polymer they can also be different polymers. When the same polymer is used the sealing includes melting and when different polymers are used the sealing is a result of expansion which forms a tight interference fit.

Residual stresses remaining in the formed part 12 and/or tube 11 can be relaxed by changing temperature causing expansion of the cross sectional size of the tube 11 and/or the part 12. The part 12 and/or the tube 11 are preferably made by an extrusion process to develop such processing memory. The changing cross sectional size of the tube 11 can provide a thicker wall section after heating and the part 12 can swell when heated. Specifically, during the heating process the tube 11 is as necessary urged axially toward the area of heating to prevent thinning which could result in an opening or tear in the tube 11. Specifically, the residual stress in the memory of the process used to make the tube 11, i.e. extrusion, could cause the tube 11 to pull apart. Urging the tube 11 is in the preferred embodiment accomplished by feeding the tube 11 axially toward the area of heating from one direction and the part 12 such as the monofilament from the other toward the middle with sufficient force to prevent thinning. The fused joint (same polymer) between the part 12 and the tube 11 is therefore uniformly around the part 12 and the seal is sufficient to plug the distal end 16 of the tube 11.

The forms 18 and 18' are preferably made of a relatively nonconductive material such as tempered glass in the preferred embodiment and the forms 18 and 18' are preferably positioned for relative movement along the axis A for placement about the part 12 as in FIG. 1 and can be placed over the tube 11 whereinside the part 12 is located as shown in FIG. 2. The forms 18 and 18' are in the preferred embodiments shaped and sized to fit the tube 11 inside surface 13 and outside surface 14, respectively and contain it. The forms 18 and 18', the tube 11 and the part 12 are preferably generally circular in cross sectional shape. The dimensions are not critical but should be selected to provide the type of fit between forms 18 or 18', the part 12 and the tube 11 desired. That is, a slip fit during initial assembly so that the tube 11 fits easily into the form 18' and the part 12 which is preferably tapered fits into the form 18 and thereafter the tube 11 to displace liquid as explained. The figures show clearance between the part 12 and the tube 11 but that is for illustration only since the fit is not loose.

A heater 19 is in the preferred embodiment made of an electrically resistive element wrapped about an outer wall 20 of the form 18 or 18' and is associated therewith for changing the temperature of the tube 11 and the part 12 therewithin sufficiently to relax residual stresses of their respective manufacturing processes used to make the tube 11 and the part 12. The heat applied will thereby cause expansion and engagement of the inside surface 13 and the part 12. The heater 19 raises the temperature beyond the glass transition point of the polymer of the tube 11 and/or the part 12 allowing the combined tube 11 and part 12 to expand to the identical cross sectional size of the internal cross section of the form 18 or 18' and to remain expanded after cooling. Melting of the polymer is not required, unless the same polymers are, as explained, used; otherwise, sealing is sufficiently accomplished when expansion takes place while the part 12 and the tube 11 are contained by the form 18 or 18'. Thus the contained expansion is adequate to create a joint 21 which will perform acceptably in connection with blood gas sensors. Expansion is for dissimilar polymers and fusion in the form of a melted heat seal occurs in between similar polymers.

A method of assembly of tube 11 with its axis along its longitude and inside and outside surfaces 13 and 14 extending between proximal and distal ends 15 or 16 over part 12 of a cross sectional shape and size to be near inside surface 13 when part 12 is at least partially within tube 11 has several steps. The method can be performed as shown in the Figures with parts of various configurations. Form 18' is shaped and sized to fit about the tube 11 outside surface 14 with heater 19 about outer wall 20 of the form 18'. The method has the step of supporting the tube 11 and the part 12 so that relative movement therebetween and along axis A places the part 12 at least partially within the tube 11. That step is followed by positioning form 18' for relative movement along axis A for placement about the tube 11 whereinside the part 12 is located to thereby contain the outside surface 14. Sufficiently changing the temperature of the tube 11 and the part 12 relaxes residual stresses of the manufacturing process used to make the tube and/or the part 12 for causing engagement of the inside surface 13 of the tube 11 and the part 12.

The method may also include the added steps of conducting sufficient heat through form 18' into the tube 11 and/or the part 12 to relax residual stresses therein with or without melting the tube 11 and/or the part 12 and clearing displaced liquid about the part 12 before heating. The step of clearing is with the preferred method performed by moving a gas along the tube 11 and the step of moving is most preferably performed by applying a vacuum to the juncture between tube 11 and part 12.

FIG. 3 is a side view in cross section of a pluralities of conductors 22 extending through a radially inwardly expanded section 23 located within the tube 11 to illustrate supporting the conductors 22 with the tube 11 as the first step in the assembly of a sensor catheter. The radially inwardly expanded section 23 of the preferred embodiment acts to support and separate the conductors of a blood gas catheter sensor. The radially inwardly expanded section 23 in FIG. 3 shows two conductors passing through respective passageways 24 formed within the tube 11. The heater 19 surrounds a form 18'' and heat applied therewith changes the temperature of the tube 11 creating the radially inwardly expanded section 23 within the tube 11 after overcoming the relaxation of residual stresses within the polymer of the tube 11 by pushing the tube axially thus feeding sufficient polymer into the radially inwardly expanding section 23. The result is that the radially inwardly expanded section 23 swells when the tube 11 expands and the conductors 22 are captured, supported and held separately in passages 24. The preferred embodiment includes conductors made of silver, platinum or gold wire, which are all good conductors of heat. Therefore, to heat properly and prevent the loss of heat to the wires; one way is to heat at just below the melting temperature of the tube 11 polymer, i.e. polyethylene and then quickly for a short time with a pulse of energy through the heating wire coil raise the temperature to melt the tube 11.

A seal may thus be provided between the tube 11, the radially inwardly expanded section 23 and the conductors 22. Specifically, during the heating process the tube 11 is as necessary urged axially toward the area of heating to provide thickening at the radially inwardly expanded section 23. Therefore an opening or tear in the tube 11 is prevented with the added material provided by feeding tube 11 into the space between the conductors 22 and the inside of the unreformed tube 11. Urging the tube 11 is in the preferred embodiment accomplished by feeding the tube 11 axially toward the area of heating from either direction; that is, each end 15 and 16 is pushed toward the middle with sufficient force to provide thickening around the conductors 22. The joint between the conductors and the tube 11 is therefore uniformly around the conductors 22 and the seal is accomplished without added cement.

An assembly, shown in FIGS. 3 and 4, is easily realized even though the dimensions of the components of the blood gas sensing catheter are small and typically microscopic. More significantly, the chemistries used for optically or electrochemically sensing blood gases may be sensitive to adhesives and so their deletion or isolation is of benefit for this reason.

In FIG. 4, a side view in cross section of the supported conductors 22 held within the radially inwardly expanded section 23 of the tube 11 illustrates how the distal end 16 thereof is plugged with the part 12 while a vacuum is drawn to clear the displaced liquid resulting when the part 12 is plugged into the tube 11. Specifically, a pipe 25 is located near the distal end 16, i.e. just outside but in position to draws a vacuum near a juncture 26 between the part 12 and tube 11 near the distal end 16 before the part 12 and the tube 11 are heated during the plugging assembly process. Arrows B illustrate the vacuum in FIG. 4. It should be appreciated that, although not preferred, a sealant can be drawn into the tube 11 to fill the proximal end 15 and that is shown by the dark areas between the conductors 22 on the left side of FIG. 4. While not specifically shown, the part 12 after being sealed in the distal end 16 as in FIGS. 2 and 4 can be cut to provide a desired shape at the plugged distal end 16. The distal seal is accomplished by first pushing the tapered plug into the tube 11 distal end 16 thus displacing liquid therein and drawing excess liquid away with vacuum. Then heating to seal the part 12 and tube 11. Thus, a completely liquid filled space is attained and no air bubbles remain.

U.S. Pat. No. 4,889,407 has an optical fiber with arrayed cells to substantially cover the cross sectional area of the fiber. An indicator sensitive to an analyte in a medium is used to determine pH and $pCO_2$ in vivo in blood. That commonly assigned patent has been incorporated herein by reference since the disclosure is applicable to that fiber distal end.

Specifically, in FIG. 5 a fiber 27 prepared in accord with the '407 patent is shown positioned coaxially within the tube 11 and expanded to the inside of the tube 11 by the heater as described hereinbefore. Cells are shown and a reflective mirror, which is the subject matter of a separate disclosure in another application having a common assignee. The fiber 27 and its tube 11 are shown being sealed together in the side view in cross section of FIG. 6. An annular space 28 surrounds a distal portion of the fiber 27.

FIG. 6 is a side view in cross section of the sealed fiber 27 and tube 11 shown removed from the glass form used to restrict radial expansion during the heating. Specifically, amid the heating process the tube 11 is as necessary urged axially toward the area of heating to prevent thinning which could result in an opening or tear in the tube. Urging the tube 11 is in the preferred embodiment accomplished by feeding the tube 11 axially toward the area of heating from either direction; that is, each end is pushed toward the middle with sufficient force to prevent thinning. The joint between the fiber 27 and the tube 11 is therefore uniformly around the fiber 27 and the seal is sufficient to maintain solution in the annular space 28 as needed.

Figure 8:
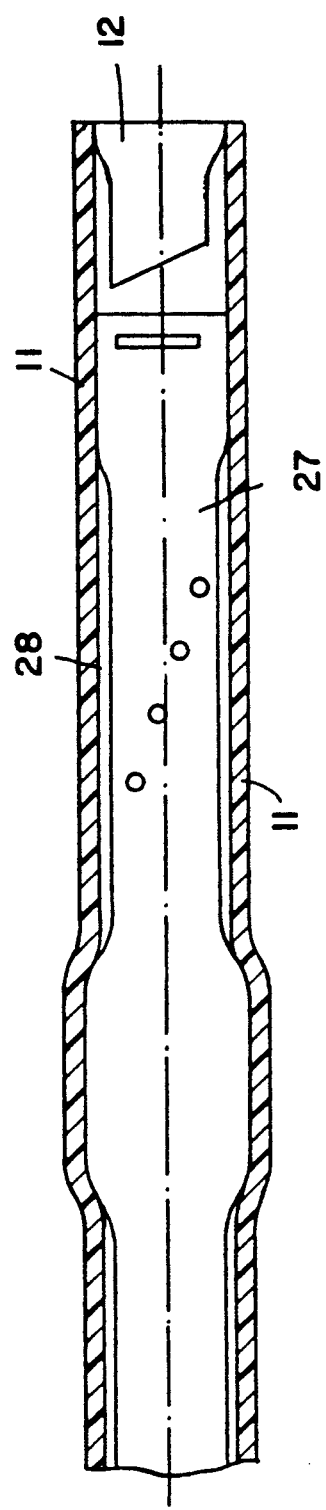
FIG. 8 is a side view in cross section of the fiber and part sealed in the tube with the space therebetween filled completely with liquid.

FIGS. 7 and 8 show a tip sealing process and apparatus similar to that disclosed in connection with FIGS. 1, 2 and 4. In these FIGS. 7 and 8 the tube 11 has the monofilament as part 12 and the plug to seal the end is also a part 12 since the concept disclosed and claimed herein is the sealing of the any such part 12 inside any part of a tube 11.

What is claimed is:

1. An apparatus for assembling a tube and a part inserted at least partially therwithin comprising:

a tube having a longitudinal axis, inside and outside surfaces, proximal and distal ends, an internal cross sectional shape identical to the part and defined by a bore therethrough and a cross sectional size larger than the part prior to changing temperature;

a part with a cross sectional shape and size to be near the inside surface of the tube when the part is at least partially within the tube and having an external cross sectional size identical to the internal cross-sectional size of the tube after change in temperature and initially a circular cross sectional shape of a diameter that allows some axial movement within the tube when there is substantially no contact with the inside surface, the part or the tube being supported so that relative movement along the axis places the part at least partially within the tube, and wherein the part is made of a thermoplastic polymer by a process that develops within the polymer thereof a memory of the unshaped thermoplastic polymer prior to forming into the cross sectional shape of the part so that residual stresses remaining in the part are relaxed by changing temperature causing expansion of the cross sectional size of the part;

a form positioned for relative movement along the axis for placement about the tube whereinside the part is located, the form shaped and sized to fit the tube outside surface and contain it, and a heater associated with the form for changing the temperature of the tube and the part sufficiently to relax residual stresses of the manufacturing processes respectively used to make the tube and the part and thereby permit engagement between the inside surface and the part.

2. An apparatus according to claim 1 wherein the process for making the thermoplastic polymer part is an extrusion process.

3. An apparatus according to claim 1, wherein the part and the tube are formed of a polymer and the heater changes the temperature beyond the glass transition point of the polymer allowing the part to expand to the external cross-sectional size identical to the internal cross sectional size of the tube and to remain expanded thereafter and engaged together.

4. An apparatus according to claim 3 wherein the form, the tube and the part are generally circular.

5. An apparatus according to claim 4 wherein the form is made of a relatively nonconductive material.

6. An apparatus according to claim 5 wherein the heater is made of an electrically resistive element wrapped about the form.

7. An apparatus according to claim 4 wherein the part is located in the tube between the ends thereof.

8. An apparatus according to claim 4 wherein the part is located in the tube near the distal of proximal end thereof.

9. An apparatus according to claim 4 wherein the part engages the tube to seal with a fluid tight juncture therebetween.

10. An apparatus for assembling a tube and a part inserted at least partially therewithin comprising:
    a polymeric circular tube with a bore therethrough along a longitudinal axis, inside and outside surfaces and proximal and distal ends;
    a part with a circular cross sectional shape and size to fit within the inside surface of the tube when the part is at least partially within the tube, the part or the tube supported so that relative movement along the axis places the part at least partially within the tube, the cross sectional size of the part having a diameter that allows axial movement of the part into the tube, the part being made of a thermoplastic polymer by a process that develops within the polymer thereof a memory of the unshaped thermoplastic polymer prior to forming into the cross sectional shape of the part;
    a form of a relatively nonconductive material shaped to circumscribe the outside surface, the form supported for relative movement along the axis for placement about the tube whereinside the part is located, the form being shaped and sized to fit the tube outside surface and contain it, and
    a heater including an electrically resistive element wrapped about the form for changing the temperature of the tube and the part sufficiently and beyond the glass transition point of their polymers to relax residual stresses of their respective manufacturing processes used to make the tube and the part and thereby cause expansion and engagement of the part and the inside surface as the tube has across sectional size larger than the part prior to changing temperature and the part has an external cross sectional size identical to the internal cross sectional size of the tube after change in temperature because the form restricts radial expansion of the outside surface.

11. A method of assembly of a tube with a longitudinal axis, inside and outside surfaces and proximal and distal ends and a part with a cross sectional shape and size to be near the inside surface of the tube when the part is at least partially within the tube using a form shaped and sized to fit about the tube outside surface and a heater associated with the form; which method comprises:
    supporting the tube or the part so that relative movement therebetween and along the tube axis places the part at least partially within the tube;
    positioning the form for relative movement along the axis for placement about the tube whereinside the part is located to thereby contain the outside surface;
    clearing displaced fluid about the junction between the part and the tube before heating;
    changing the temperature of the tube and the part sufficiently to relax residual stresses of the manufacturing process respectively used to make the tube and the part for causing engagement of the inside surface of the tube and the part; and
    conducting sufficient heat through the form into the part to relax residual stresses therein to cause engagement between the part and the tube.

12. A method according to claim 11 wherein the clearing of displaced fluid is performed by moving a gas about the space.

13. A method according to claim 12 wherein the gas is moved by applying a vacuum near the space.

14. An assembly of a tube and a part inserted at least partially therewithin comprising:
    a circular tube with a bore therethrough a longitudinal axis, inside and outside surfaces, proximal and distal ends, and an internal circular cross sectional shape;
    a part with a circular cross sectional shape and size to fit within the inside surface of the tube when the part is at least partially within the tube, the part made of a thermoplastic polymer by a process that develops within the polymer thereof a memory of the unshaped thermoplastic polymer prior to forming into the cross sectional shape of the part so that residual stresses remaining in the part are relaxed by changing temperature causing expansion of the cross sectional size of the part by exceeding the glass transition point of the polymer to relax residual stresses of the manufacturing extrusion process used to make the part and thereby cause the part to engage the inside surface of the tube so the internal cross sectional size of the part remains expanded and engaged against the tube after the change in temperature, the part being between the ends of the tube or at an end of the tube, wherein the tube is extruded thermoplastic polymer so that relaxation of residual stresses by change in temperature causes the inside surface thereof to move toward the part for engagement.

15. An assembly according to claim 14 wherein the tube has conductors passing therewithin so that relaxation of residual stresses by change in temperature coupled with urging the tube toward where it is heated causes the inside surface thereof to become a radially inwardly expanded section that engages the conductors for supporting them in passages created thereby and holds in space apart relation.

* * * * *